US006534013B1

(12) United States Patent
Kennedy

(10) Patent No.: US 6,534,013 B1
(45) Date of Patent: Mar. 18, 2003

(54) MICROFLUIDIC DEVICES AND SYSTEMS

(75) Inventor: Colin B. Kennedy, Mill Valley, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/504,301

(22) Filed: Feb. 15, 2000

Related U.S. Application Data

(63) Continuation of application No. 09/190,428, filed on Nov. 12, 1998, now Pat. No. 6,048,498, which is a continuation of application No. 08/906,441, filed on Aug. 5, 1997, now Pat. No. 5,876,675.

(51) Int. Cl.[7] .................................................. B01L 3/00
(52) U.S. Cl. ...................... 422/99; 422/82.05; 422/100; 422/104; 204/601; 204/603; 73/864.91
(58) Field of Search ........................... 422/55, 58, 68.1, 422/82.05, 99, 100, 104; 204/601, 603; 73/864.91

(56) References Cited

U.S. PATENT DOCUMENTS

| | | | |
|---|---|---|---|
| 4,038,149 A | | 7/1977 | Liner et al. |
| 4,390,403 A | | 6/1983 | Batchelder |
| 4,908,112 A | | 3/1990 | Pace |
| 5,126,022 A | | 6/1992 | Soane et al. |
| 5,156,285 A | | 10/1992 | Zogg et al. |
| 5,484,731 A | | 1/1996 | Stevens |
| 5,486,335 A | | 1/1996 | Wilding et al. |
| 5,498,392 A | * | 3/1996 | Wilding et al. ............ 422/102 |
| 5,571,410 A | | 11/1996 | Swedberg et al. |
| 5,585,069 A | | 12/1996 | Zanzucchi et al. |
| 5,593,838 A | | 1/1997 | Zanzucchi et al. |
| 5,603,351 A | | 2/1997 | Cherukuri et al. |
| 5,635,358 A | | 6/1997 | Wilding et al. |
| 5,635,403 A | | 6/1997 | Bailey |
| 5,637,469 A | | 6/1997 | Wilding et al. |
| 5,750,015 A | | 5/1998 | Soane et al. |
| 5,955,028 A | * | 9/1999 | Chow ........................ 422/63 |

FOREIGN PATENT DOCUMENTS

| | | |
|---|---|---|
| WO | WO 9604547 | 2/1996 |
| WO | WO 9702357 | 1/1997 |

OTHER PUBLICATIONS

Dasgupta, P.K. et al., "Electroosmosis: A Reliable Fluid Propulsion System for Flow Injection Analysis," *Anal. Chem.* 66:1792–1798 (1994).
Jacobson, S.C. et al., "Fused Quartz Substrates for Microchip Electrophoresis," *Anal. Chem.* 67:2059–2063 (1995).
Manz, A. et al., "Electroosmotic pumping and electrophoretic separations for miniaturized chemical analysis systems," *J. Micromech. Microeng.* 4:257–265 (1994).
Ramsey, J.M. et al., "Microfabricated chemical measurement systems," *Nature Med.* 1:1093–1096 (1995).
Seiler, K. et al., "Planar Glass Chips for Capillary Electrophoresis: Repetitive Sample Injection, Quantitation, and Separation Efficiency," *Anal. Chem.* 65:1481–1488 (1993).
Seiler, K. et al., "Electroosmotic Pumping and Valveless Control of Fluid Flow Within a Manifold of Capillaries on a Glass Chip," *Anal. Chem.* 66:3485–3491 (1994).
Young, J., "Lab on a Chip," *Forbes* Sep. 23, 1996.

* cited by examiner

Primary Examiner—John Kim
(74) Attorney, Agent, or Firm—Andrew L. Filler; Matthew B. Murphy

(57) ABSTRACT

The present invention is generally directed to improved microfluidic devices and systems, and particularly to a microfluidic device which comprises a planar body structure, at least a first channel network comprising intersecting channels disposed within the body structure wherein the first channel network is contained within an area of the planar body structure that is less than about 6 cm$^2$; and a holder assembly configured to receive the body structure, the holder assembly having at least one aperture disposed therethrough from an upper surface to a lower surface thereof, and wherein the body structure is fixedly mounted to the holder assembly.

16 Claims, 4 Drawing Sheets

MICROFLUIDIC DEVICES AND SYSTEMS

CROSS REFERENCE TO RELATED APPLICATION

This application is a continuation of U.S. patent application Ser. No. 09/190,428, filed Nov. 12, 1998, U.S. Pat. No. 6,048,498, which is a continuation of U.S. patent application Ser. No. 08/906,441, filed Aug. 5, 1997, now U.S. Pat. No. 5,876,675.

BACKGROUND OF THE INVENTION

Microfluidic systems have been previously described for carrying out a number of operations, including, e.g., capillary electrophoresis (Manz et al., J. Chromatog. 593:253–258 (1992)), gas chromatography (Manz et al., Adv. In Chromatog. 33:1–66 (1993)), cell separations (U.S. Pat. No. 5,635,358) and the like. Generally, such devices have been described in the context of proof-of-concept experiments, where they have been used in operations primarily performed by highly skilled technicians. Despite the advancements made with respect to these devices, however, such devices have not been adapted for use by less sophisticated operators.

In particular, the microfluidic devices and systems for controlling and monitoring the devices described to date, have generally included bulky, complex and expensive prototypical systems whose use requires complex series of operations and or a high level of skill on the part of the operator. Further, such systems are generally fabricated in the lab, where time and funding can be at a premium, resulting in little or no attention being given to features of the device that are not specifically directed to the fluidic elements. As such, these devices tend to be extremely sensitive to operator handling, and by implication, operator error. It would therefor be desirable to provide microfluidic devices and/or systems which are more "user friendly," i.e., more resistant to operator error, and particularly, operator handling error. The present invention meets these and other needs.

SUMMARY OF THE INVENTION

The present invention generally provides improved microfluidic devices, apparatus and systems which reduce the potential for errors which arise from operator mishandling of such devices. In particular, the present invention provides microfluidic devices which comprises a substrate having a first surface and at least one edge, at least two intersecting microscale channels disposed in the substrate, and a detection window in the first surface which permits transmission of an optical signal from at least one of the at least two intersecting channels. These devices also comprise a manual handling structure attached to the substrate for handling the microfluidic device substantially without contacting the first surface of the substrate. Also provided are apparatus for utilizing these devices, which apparatus include electrical control systems for applying an electric field across each of the at least first and second intersecting channels within the device, as well as optical detectors disposed adjacent to the detection window within the device for receiving the optical signal.

DETAILED DESCRIPTION OF THE INVENTION

Figure 1:
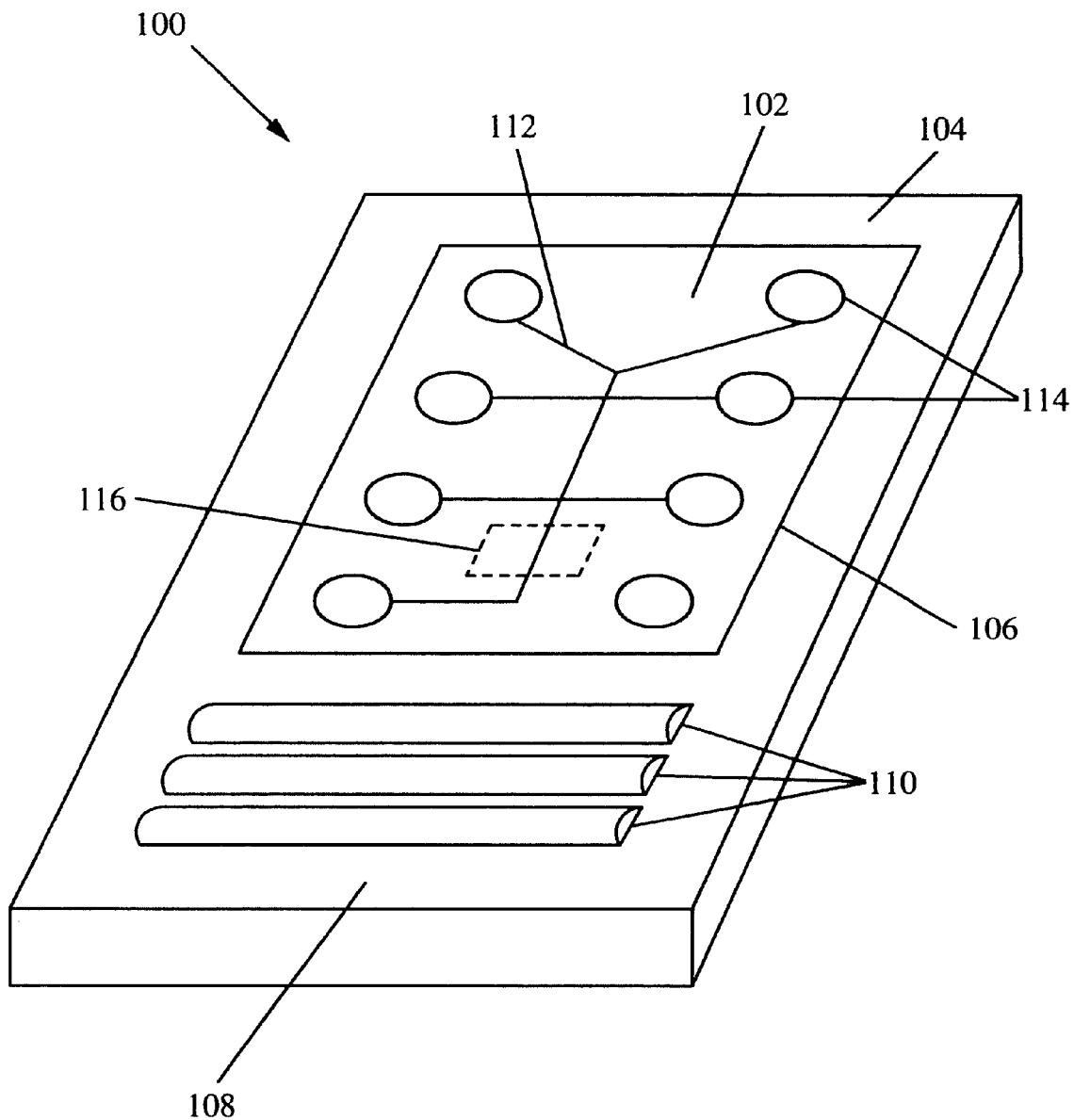
FIG. 1 schematically illustrates an embodiment of a microfluidic device incorporating a manual handling structure.

The present invention is generally directed to improved microfluidic devices and systems, and particularly, microfluidic devices that are easier to handle by the operator, without damaging, contaminating or otherwise fouling, as a result of manual contact with the device. Specifically, the present invention provides microfluidic devices and systems which include manual handling structures, for allowing easy handling of the small scale devices with minimal potential for fouling as a result of manual contact with the device. As noted above, previously, microfluidic devices have been used mainly in "proof of concept" applications, by highly skilled researchers for extremely low throughput applications, e.g., single sample separations etc. Because of the nature of this use, it has been largely unnecessary to provide microfluidic devices with elements to reduce or prevent operator error or mishandling. Specifically, because such devices were used by highly skilled researchers, the chances of their becoming damaged by operator error or mishandling were reduced. Similarly, because these devices had been used primarily in such "proof-of-concept" research, e.g., involving low throughput or single sample assays, they were generally considered disposable, somewhat obviating the need for significant barriers to mishandling and the like.

The microfluidic devices according to the present invention, on the other hand, are generally intended to be used by the ordinary research and development consumer, e.g., laboratory technicians, physicians in point of care diagnostic applications, in home testing, and the like. As such, the devices must generally be designed to withstand or prevent a certain level of consumer mishandling. Of particular relevance is mishandling due to excessive contact with the microfluidic device by the operator. For example, because microfluidic devices include channels having extremely small cross-sectional dimensions, e.g., regularly in the range of from 1 to 15 $\mu$m, these devices are extremely vulnerable to fouling as a result of dirt, dust or other particulate matter which can be deposited in the reservoirs of the device and potentially block one or more of the channels of the device.

Further, in addition to fouling the interior portions of these devices, direct contact by a user with the surface of the microfluidic device can have a number of additional adverse effects. For example, the devices of the present invention typically include a detection window for observing or optically detecting the results of the operation of the device, e.g., assay results. Often such optical detection methods rely upon highly sensitive instruments, detectors and the like. Accordingly, any interference resulting from the collection of dirt or oils on this detection window can adversely effect the amount or quality of the signal that is transmitted by the window and detected by the detector.

Similarly, collection of dirt and oils on the surface of the microfluidic devices can provide surface locations at which moisture may condense during the operation of the device. Such moisture and condensation can provide an avenue for the contamination of the device, or cross contamination among the various fluid access ports or wells of the device. Further, and perhaps more critically, the formation of this condensation on the surface of an microfluidic device which employs an electrokinetic-based material transport and direction system can also lead to electrical shorting between adjacent reservoirs/electrodes used in these systems, e.g., as used in preferred aspects of the present invention. Such shorting can significantly reduce and even destroy the efficacy of these material direction and transport systems.

The problems associated with handling the microfluidic devices are compounded by the small size of these devices. In particular, because the microfluidic devices described herein have relatively small external dimensions, it is substantially more difficult to handle such devices without contacting large portions of the surface of the device. Further, improvements in fluid direction systems, e.g., electroosmotic systems, have permitted a substantial reduction n the size of microfluidic devices. As these devices shrink in size, it becomes more and more difficult to handle them, without contacting a substantial portion of their surfaces, potentially leading to the problems described.

By providing a means of manually handling or holding the device without contacting the surface of the device in which the reservoirs are disposed, one can substantially reduce the probability that dirt or dust might find its way into the reservoirs and channels of the device. Such dust and dirt can readily foul microfluidic channels which typically include at least one cross sectional dimension as small as 0.1 to 10 $\mu$m, and typically in the range from about 5 $\mu$m to about 100 $\mu$m. Further, these manual handling structures, prevent contact by the user or operator with the relevant surfaces of the device, and thereby significantly reduce the probability that any surface contamination of the device will occur, which contamination could potentially lead to shorting and/or interference with the detection window.

As used herein, the term "microfluidic," or the term "microscale" when used to describe a fluidic element, such as a passage, chamber or conduit, generally refers to one or more fluid passages, chambers or conduits which have at least one internal cross-sectional dimension, e.g., depth or width, of between about 0.1 $\mu$m and 500 $\mu$m. In the devices of the present invention, the microscale channels preferably have at least one cross-sectional dimension between about 0.1 $\mu$m and 200 $\mu$m, more preferably between about 0.1 $\mu$m and 100 $\mu$m, and often between about 0.1 $\mu$m and 20 $\mu$m. Accordingly, the microfluidic devices or systems of the present invention typically include at least one microscale channel, and preferably at least two intersecting microscale channels disposed within a single body structure.

The body structure typically comprises an aggregation of separate parts, e.g., capillaries, joints, chambers, layers, etc., which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device. In preferred aspects, the bottom portion will comprise a solid substrate that is substantially planar in structure, and which has at least one substantially flat upper surface. A variety of substrate materials may be employed as the bottom portion. Typically, because the devices are microfabricated, substrate materials will generally be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, particularly where electric fields are to be applied.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such substrates are readily manufactured from microfabricated masters, using well known molding techniques, such as injection molding, embossing or stamping, or by polymerizing the polymeric precursor material within the mold. Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. Pat. No. 5,885,470, and which is incorporated herein by reference in its entirety for all purposes.

The channels and/or chambers of the microfluidic devices are typically fabricated into the upper surface of the substrate, or bottom portion, using the above described microfabrication techniques, as microscale grooves or indentations. The lower surface of the top portion of the microfluidic device, which top portion typically comprises a second planar substrate, is then overlaid upon and bonded to the surface of the bottom substrate, sealing the channels and/or chambers (the interior portion) of the device at the interface of these two components. Bonding of the top portion to the bottom portion may be carried out using a variety of known methods, depending upon the nature of the substrate material. For example, in the case of glass substrates, thermal bonding techniques may be used which employ elevated temperatures and pressure to bond the top portion of the device to the bottom portion. Polymeric substrates may be bonded using similar techniques, except that the temperatures used are generally lower to prevent excessive melting of the substrate material. Alternative methods may also be used to bond polymeric parts of the device together, including acoustic welding techniques, or the use of adhesives, e.g., UV curable adhesives, and the like.

In accordance with the present invention, the microfluidic devices and/or systems include a manual handling structure. By "manual handling structure" is meant a structural element that is attached to or an integral part of the microfluidic device or system, which facilitates the manual handling of the device or system, and prevents excess contact between the handler and the microfluidic device, per se. The holding structures may be fabricated as an integrated portion of the microfluidic device, e.g., as an extension of the device's body structure, or alternatively may comprise a separately fabricated structure that is attached to the microfluidic device, either permanently or removably. In the latter instance, the handling structure may be fabricated as a portion of a separate holder assembly, into which the microfluidic device is permanently or removably inserted. In either event, the microfluidic device is securely inserted into the holder assembly. Typically, such holding structures will be fabricated from a polymeric material, e.g., polystyrene, polypropylene, or the other polymeric materials described herein. These materials are selected, again for their inertness to the various reagents, temperatures or other conditions to which the overall device might be subjected.

By reducing or preventing contact with the device, the manual handling structures described herein, serve to prevent fouling of the device resulting from excess handling of the device. For example, in a first aspect, the manual handling structures prevent the deposition of debris, e.g., dirt, dust or other detritus, on the surface of the device resulting from manual contact with that surface. Such debris can be deposited within the wells or reservoirs of the device, and can potentially clog or otherwise interfere with flow within the channels of the device. This is a particular hazard for devices which include large numbers of ports or reservoirs, providing greater opportunity for debris to find is way into the channel elements. These include those devices intended for the analysis of multiple samples, which devices can include upwards of 8, 12, 16 and even 18 or more reservoirs or ports.

As noted previously, the manual handling structures, as described in terms of the present invention, provide the most significant advantage in microfluidic devices which utilize either or both of electrical material direction/transport systems, and optical detection methods and systems.

In preferred aspects, the devices, methods and systems described herein, employ electrokinetic material transport systems, and preferably, controlled electrokinetic material transport systems. As used herein, "electrokinetic material transport systems" include systems which transport and direct materials within an interconnected channel and/or chamber containing structure, through the application of electrical fields to the materials, thereby causing material movement through and among the channel and/or chambers, i.e., cations will move toward the negative electrode, while anions will move toward the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner.

Although described for the purposes of illustration with respect to a four way, cross intersection, these controlled electrokinetic material transport systems can be readily adapted for more complex interconnected channel networks, e.g., arrays of interconnected parallel channels.

The incorporation of manual handling structures prevents the deposition of fluids, dirt and oils from the operators hands or other handling equipment, which may affect the level of condensation on the surface of the microfluidic device. Such condensation can eliminate the electrical isolation between adjacent wells on the microfluidic device, effectively shorting out the material transport system. Additional measures may also be provided to avoid this condensation, including application of hydrophobic coatings on the surface of the device, e.g., polytetrafluoroethylene (TEFLON™), and the like.

Also as noted previously, the microfluidic devices incorporating manual handling structures are particularly advantageous where these microfluidic devices incorporate or are utilized with optical detection systems. Such devices typically include, fabricated into their structure, an optical detection window fabricated across one of the plurality of channels within the device, whereby an analyte traveling within that channel is detected by virtue of an optical characteristic or label. The detection window may comprise a portion of the substrate material, where that material is transparent, e.g., glass, quartz, or transparent polymeric substrates. Alternatively, for opaque substrates, or substrates which have excessive background signals (e.g., fluorescence), detection windows fabricated from an appropriate transparent material, e.g., glass, quartz and the like, may be introduced into the structure of the device, across the channel in question.

In operation, an optical detector is positioned adjacent to the detection window whereby the detector senses the presence or absence of the optical characteristic within the channel. Examples of such optically detectable labels include, e.g., colored labels, colloid labels, fluorescent labels, e.g., fluorescein, rhodamine, etc., and chemiluminescent labels. The optical detector may be any of a variety of optical detection systems, e.g., fluorescent, colorimetric or video detection systems. For example, for fluorescence based analyses, the optical detector will typically include an excitation light source, e.g., a laser or LED, collection optics for collecting fluorescence from the sample and separating that fluorescence from the reflected excitation light, and detectors, such as photodiodes and/or photomultiplier tubes, for detecting, quantifying and/or recording the amount of fluorescence from the channel. Alternate detectors include, e.g., CCDs (charged coupled devices) disposed adjacent the channel and coupled to monitoring/recording equipment, for monitoring and recording the analyte level in the channel.

Because these devices and systems are used in relatively precise analyses, any interference with the optical detection of analytes within the device can have substantial detrimental effect on the results of such analyses. In particular, any dirt, oil or other debris which deposits upon the detection window can interfere with the accurate detection of analyte within the channel. The manual handling structures of the present invention provide a means of handling these devices without contacting the detection window, thereby reducing the probability of any such optical contamination occurring.

In addition to the foregoing, and as noted above, the manual handling structures described herein are also particularly useful in conjunction with very small scale microfluidic devices. For example, in preferred aspects, the handling structures are provided on microfluidic devices that have internal, intersecting channel networks disposed within a planar body structure, where the entire microscale channel network of the device falls, i.e., the layout of intersecting channels, within a very small area of the planar device structure which area is typically less than 6 cm$^2$, preferably less than 5 cm$^2$, more preferably less than 4 cm$^2$, still more preferably less than 3 cm$^2$, and often, less than 2 cm$^2$ or even 1 cm$^2$. Thus, typically, all of the channels of the device are fabricated into the surface of the lower substrate within a region having the area described. In the case of rectangular or square shaped devices, the layout of the intersecting channel structure will typically fall within a region having dimensions less than from about 2.5 cm by about 2.5 cm, preferably less than about 2 cm by about 2 cm, more preferably, less than about 1.5 cm by about 1.5 cm, and in some cases, less than about 1 cm by about 1 cm.

One example of a manual handling structure according to the present invention is shown in FIG. 1. As shown the microfluidic system 100 includes a microfluidic substrate 102, mounted in a holder assembly 104. As shown, the microfluidic device includes within its structure, a plurality of intersecting channels 112 which include at their unintersected termini, a plurality of reservoirs, wells or ports 114 for introduction of fluids into the interior portion of the device, as well as providing electrical contact/access to the fluid within the channels. A detection window 116 is also shown disposed across one f the channels 112, which detection window is capable of transmitting an optical signal from the channel to a detector. The holder assembly shown, comprises a planar structure having a first surface with a cavity disposed therein. The cavity 106 is sized or adapted to fit the substrate in a secure, fixed fashion, e.g., such that the device does not freely fall out of the holder assembly, e.g., when inverted. Typically, an aperture is provided through the holder assembly such that when the substrate/microfluidic device is inserted into the holder, the detection window 112 is placed over the aperture. This allows the free transmission of light through the detection window 116 and the remainder of the device for optical detection. For example, a light source may be placed above the substrate and directed at one of the channels in the device. Light passing through the channel and the device then proceeds through the aperture in the holder assembly and reaches a detector disposed below the device. In some instances, the substrate may be permanently affixed to the holder assembly, e.g., using adhesives, or in the case of polymeric substrates, through the use of solvent bonding, acoustic welding or thermal bonding techniques.

The holder assembly extends in one dimension from an edge of the substrate/microfluidic device, i.e., from the edge of the cavity into which the microfluidic device is inserted, providing a flat planar surface 108, upon which are fabricated a plurality of raised ridges 110. The surface 106 and ridges 108 provide a gripping surface for manually handling the microfluidic device substantially without actually contacting the surface of the substrate/microfluidic device, i.e., contacting less than 25% of the surface, preferably, less than 10% of the surface and often less than 5% of the substrate surface. A variety of other surface textures may similarly or alternatively be provided upon the surface of the handling structure in the place of raised ridges, such as knurling, raised bumps, surface roughing and the like. Similarly, rubber holder assemblies, or rubber handling structures attached to the holder assemblies may also be used to provide a suitable gripping surface, e.g., particularly in wet processes.

Figure 2:
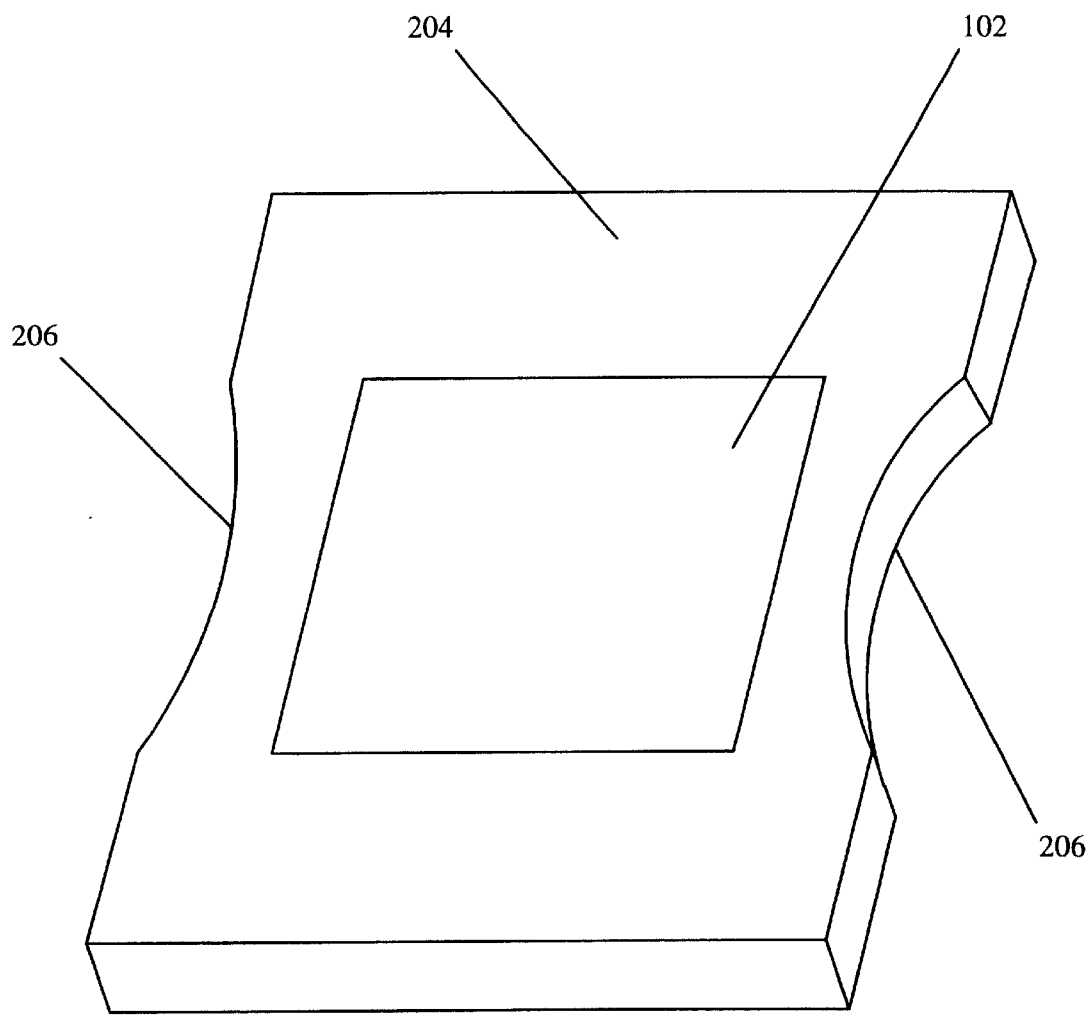
FIG. 2 schematically illustrates an alternate embodiment of a microfluidic device incorporating a manual handling structure.

Another example of manual handling structure according to the present invention, is shown from a perspective view in FIG. 2. As shown, the planar microfluidic substrate 102 (channels and reservoirs not shown), is again inserted into a holder assembly 204 such that at least its top surface is exposed, e.g., providing access to the ports/reservoirs, for fluid introduction and electrode access. Typically, the bottom surface of the device is also exposed, i.e., not covered by the holder assembly. This permits access to the bottom surface of the device, i.e., optical access for the detector, thermal access for a heating or cooling element or heat sink, e.g., a resistive heater, peltier cooler or the like. The holder assembly includes inwardly tapered or inset edges 206, at opposing edges of the device, for manually holding the overall device without substantially contacting either of the top or bottom surfaces of the microfluidic device. Although not shown, the edges of the device may also include raised ridges to provide an adequate gripping surface for the overall device. In addition, although the substrate portion of the device is shown having a particular shape, e.g., a planar rectangle or square, it will be readily appreciated that a variety of substrate shapes may be used, including disks, i.e., circles, triangles etc. As such, the above description, in referring to a device having two opposite edges, also encompasses those embodiments having edges that are substantially opposite to each other in the planar structure despite the fact that such a device may not include two separate and distinct edges. For example, although a device having a planar, circular shape has but one edge, two portions of that edge may be opposite each other in the planar structure of the device, and would therefor fall within the description provided herein for a structure having at least two opposing or opposite edges.

Figure 3A:
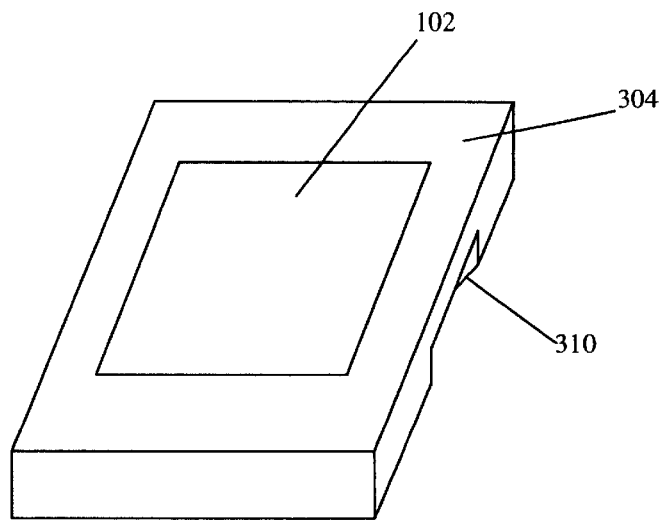
FIGS. 3A, 3B, and 3C schematically illustrates a further embodiment of a microfluidic device incorporating a manual handling structure (from perspective, top, and bottom views, respectively).
Figures 3B, 3C:
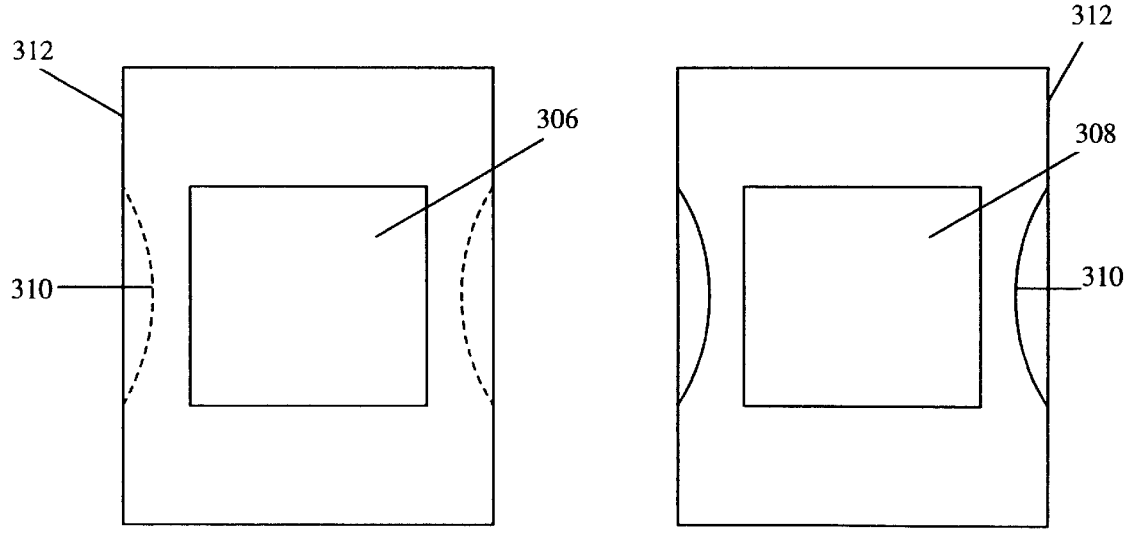
Figure 4:
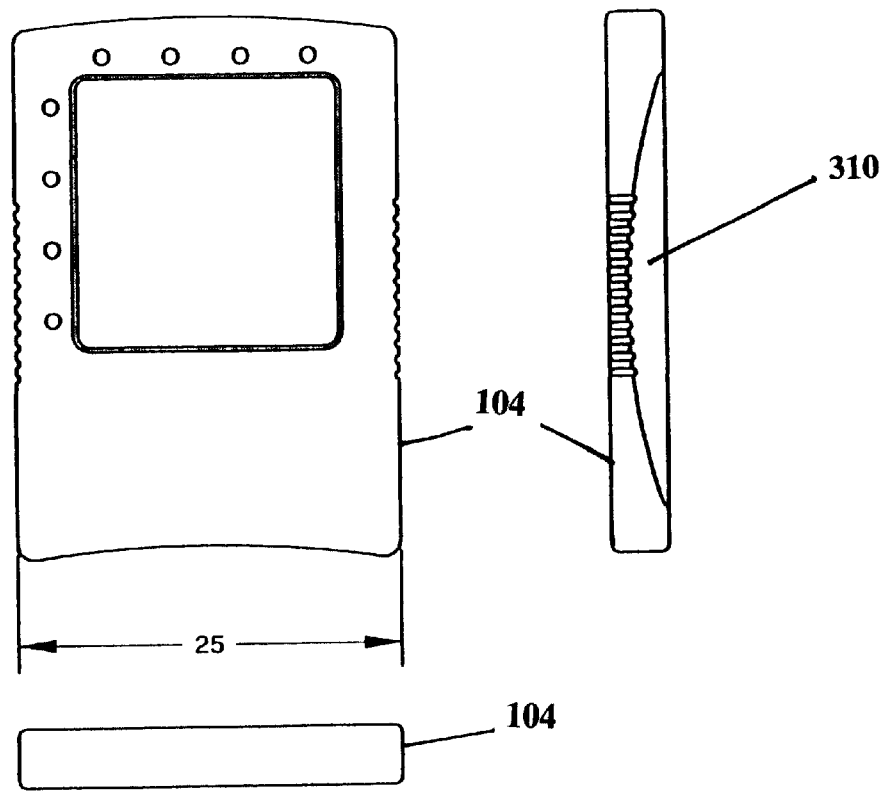
FIG. 4 illustrates an ornamental design for a microfluidic device, which also incorporates a manual handling structure.
Figure 4:
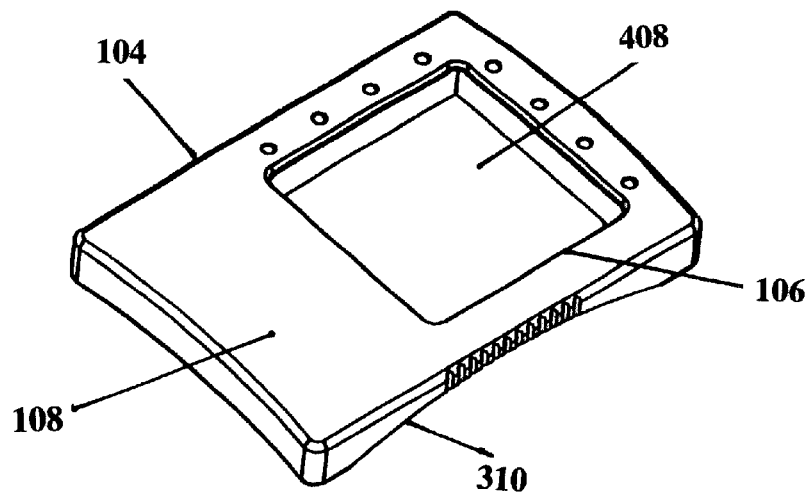

A similar, related example of a manual handling structure according to the present invention is shown in FIG. 3, from a perspective view (FIG. 3A), a top view (FIG. 3B) and a bottom view (FIG. 3C). Again, as shown, the microfluidic substrate 102 (reservoirs and channels not shown) is inserted into a holder assembly 304, such that the top and bottom surfaces 306 and 308 of the substrate are exposed. As with the holder assembly shown in FIG. 2, the device shown in FIG. 3 also includes beveled or chamfered edges 310 as the manual handling structure. As shown, the beveled or chamfered edges 310 of the holder assembly only extend up a portion of the side edges 312 of the assembly. This permits the added advantage of providing a lip portion of the device which allows one to lift the overall device when it is sitting flatly on a flat surface, or mounted in a further holding structure, e.g., a nesting well in a controller, scanner, or fabrication device. A related design for a microfluidic device housing, including a manual handling structure is shown in FIG. 4. Again, although FIG. 4 illustrates a housing into which a separate device is inserted, it will be readily appreciated that the housing element may be manufactured as an integral part of the device, e.g., as an extended portion of the body structure of the device.

In addition to the manual handling structures described above, the devices of the present invention may also include other structural elements to facilitate their handling and use. For example, the devices may include alignment structures to ensure proper insertion of the device into the instrumentation used in the device's operation, e.g., electrical controllers, detectors, filling systems, sample introduction systems and related instrumentation. Alignment of the microfluidic devices within these instruments is important to ensure the proper alignment of the device for: (1) receiving electrodes, for electrical fluid direction systems; (2) for properly positioning the reservoirs for introduction of fluids and samples, e.g., for receipt of the fluid introduction conduits, i.e., pipette tips; and (3) for proper alignment of the detection window of the device in front of the detector. Such alignment structures may comprise one or more of a number of different structural elements. For example, alignment holes or pins may be provided upon the device such that the holes or pins align with corresponding, complementary pins or holes on the instrumentation. Alternatively, sides or edges of the device may incorporate structural features, e.g., notches, tabs, cropped corners, bevels, ridges and the like, which are complementary to structural features on the instrumentation, e.g., in a nesting well for the controller and/or scanning device.

For those devices which are intended for use with multiple samples, e.g., having multiple sample introduction reservoirs, wells or ports, the devices may also include indexing elements, for identifying the various sample introduction wells. For example, in the case of rectangular or square devices, such indexing elements can include marks, notches, or alphanumeric symbols disposed along one edge of the device (on one axis), e.g., on the device itself or on the holder assembly adjacent to the device, which marks or symbols are aligned with each row of sample reservoirs or wells. A second set of marks or symbols may be provided on a second edge of the device adjacent the first (on the other axis).

By reducing the actual contact the user has with the microfluidic device, as well as ensuring the proper use of the device, all of the above described features cooperate to prevent or reduce the possibility of operator mishandling of the microfluidic devices described herein, and particularly that mishandling which results from excessive contact with the relevant surfaces of the device.

Although the present invention has been described in some detail by way of illustration and example for purposes of clarity and understanding, it will be apparent that certain changes and modifications may be practiced within the scope of the appended claims. All publications, patents and patent applications referenced herein are hereby incorporated by reference in their entirety for all purposes as if each such publication, patent or patent application had been individually indicated to be incorporated by reference.

What is claimed is:

1. A microfluidic device, comprising:
   a planar body structure;
   at least a first channel network comprising intersecting channels disposed within the body structure;
   wherein the first channel network is contained within an area of the planar body structure that is less than about 6 cm$^2$; and
   a holder assembly configured to receive the body structure, the holder assembly having at least one aperture disposed therethrough from an upper surface to a lower surface thereof, and wherein the body structure is fixedly mounted to the holder assembly.

2. The microfluidic device of claim 1, wherein the first channel network is contained within an area of the planar body structure that is less than about 5 cm$^2$.

3. The microfluidic device of claim 1, wherein the first channel network is contained within an area of the planar body structure that is less than about 4 cm$^2$.

4. The microfluidic device of claim 1, wherein the first channel network is contained within an area of the planar body structure that is less than about 3 cm$^2$.

5. The microfluidic device of claim 1, wherein the first channel network is contained within an area of the planar body structure that is less than about 2 cm$^2$.

6. The microfluidic device of claim 1, wherein the first channel network is contained within an area of the planar body structure that is less than about 1 cm$^2$.

7. The microfluidic device of claim 1, wherein the body structure comprises a square or rectangular shape having dimensions less than from about 2 cm by about 2 cm.

8. The microfluidic device of claim 1, wherein the body structure comprises a square or rectangular shape having dimensions less than from about 1.5 cm by about 1.5 cm.

9. The microfluidic device of claim 1, wherein the body structure comprises a square or rectangular shape having dimensions less than from about 1 cm by about 1 cm.

10. The microfluidic device of claim 1, wherein the body structure comprises a plurality of reservoirs disposed in a surface of the body structure, the plurality of reservoirs being in fluid communication with the at least first channel network.

11. The microfluidic device of claim 10, wherein the plurality of reservoirs are in communication with unintersected termini of the intersecting channels.

12. The microfluidic device of claim 1, wherein:

the body structure comprises upper and lower planar substrate layers;

the intersecting channels of the first channel network are fabricated as a plurality of grooves on a surface of the lower substrate; and the upper planar substrate layer is overlaid and bonded to the lower planar substrate layer to seal the plurality of grooves to form the first channel network.

13. The microfluidic device of claim 12, wherein at least one of the upper and lower planar substrate layers is selected from a group consisting of glass, quartz, and a polymeric material.

14. The microfluidic device of claim 1, wherein the holder assembly comprises a cavity, the cavity being sized to fixedly receive the body structure.

15. The microfluidic device of claim 1, wherein the holder assembly comprises at least a first alignment structure for aligning the microfluidic device on a detector instrument.

16. The microfluidic device of claim 1, wherein the holder assembly comprises a polymeric holder assembly.

* * * * *